United States Patent
Mallart

[19]

[11] Patent Number: 5,932,807
[45] Date of Patent: Aug. 3, 1999

[54] DEVICE FOR THE NON-DESTRUCTIVE TESTING OF HOLLOW TUBULAR OBJECTS BY MEANS OF ULTRASOUND

[75] Inventor: Raoul Mallart, Paris, France

[73] Assignee: U.S. Philips Corporation, New York, N.Y.

[21] Appl. No.: 08/548,157

[22] Filed: Oct. 25, 1995

[30] Foreign Application Priority Data

Oct. 25, 1994 [FR] France .................................. 94 12755

[51] Int. Cl.⁶ .................................................. G01N 29/04
[52] U.S. Cl. ................................................ 73/641; 73/628
[58] Field of Search ............................. 73/618, 619, 620, 73/622, 624, 625, 626, 628, 641, 623

[56] References Cited

U.S. PATENT DOCUMENTS

| | | | |
|---|---|---|---|
| 4,002,382 | 1/1977 | Beaver ........................................ | 73/626 |
| 4,011,750 | 3/1977 | Robinson ................................... | 73/628 |
| 4,070,905 | 1/1978 | Kossoff ...................................... | 73/641 |
| 4,170,142 | 10/1979 | Posakony ................................... | 73/641 |
| 4,279,157 | 7/1981 | Schomberg ............................... | 73/618 |
| 4,497,210 | 2/1985 | Uchida ...................................... | 73/619 |
| 4,550,606 | 11/1985 | Drost ......................................... | 73/626 |
| 4,671,115 | 6/1987 | Ogawa ...................................... | 73/641 |
| 5,060,651 | 10/1991 | Kondo ....................................... | 73/625 |
| 5,226,847 | 7/1993 | Thomas, III .............................. | 73/623 |
| 5,271,406 | 12/1993 | Ganguly et al. . | |
| 5,331,855 | 7/1994 | Takashita .................................. | 73/625 |

FOREIGN PATENT DOCUMENTS 0396761 11/1990 European Pat. Off. .

OTHER PUBLICATIONS

D.F. Loy & J.A. Vano, "Vessel Nozzle Inner Radius Examinations Using Ultrasonic Time–Of–flight Diffraction (TOFD)", EPRI, Vessel & Internals Inspection Conference, San Antonio, TX, Jul. 11–15, 1994.

*Primary Examiner*—Christine K. Oda
*Attorney, Agent, or Firm*—Anne E. Barschall

[57] ABSTRACT

A device for the non-destructive testing of hollow tubular objects using ultrasound. The device has a stage for transmission of ultrasonic waves and a stage for reception of ultrasonic signals. The transducer structure includes an assembly of annular individual transducers which are juxtaposed in a coaxial fashion or, in an alternative embodiment, two annular arrays, each of which consists of an assembly of juxtaposed individual transducers. Moreover, the stages for the transmission and reception can simultaneously select, from the assembly or from each of the assemblies, at least one transmitter transducer (2(I)) and at least one receiver transducer (2(j)). This selection forms a transducer sub-assembly which can be displaced at will by electronic scanning along the axis of the succession of transducers in order to enable optimum execution of the so-called TOFD testing method.

27 Claims, 4 Drawing Sheets

DEVICE FOR THE NON-DESTRUCTIVE TESTING OF HOLLOW TUBULAR OBJECTS BY MEANS OF ULTRASOUND

The present invention relates to a device for the non-destructive testing of hollow tubular objects by means of ultrasound, comprising a transducer structure which is connected to a stage for the transmission of ultrasonic waves for excitation of the transducer structure and to a stage for reception of ultrasonic signals by the structure.

The invention also relates to an ultrasonic transducer structure which is suitable for connection to a non-destructive testing device of this kind.

BACKGROUND OF THE INVENTION

Ultrasonic techniques are of prime importance in the field of non-destructive testing of materials as they enable evaluation of some of their properties and particularly detection of discontinuities present therein. The object testing techniques especially concerned are those which utilize two distinct transducers which are both situated to the same side of the object to be examined, one transducer acting as a transmitter and the other as a receiver, between the transducers there being provided an ultrasonic wave propagation which is variable in conformity with the presence or absence of discontinuities. These techniques are referred to as pitch and catch techniques and are classified in two categories which are referred to as direct and indirect categories.

According to the direct technique, illustrated in FIG. 1 in which $E_1$ designates the transmitter transducer, the receiver transducer $R_1$ is arranged in the location in which the ultrasonic beam reflected by the back of the object M being tested is actually expected in the absence of any discontinuity in this object. In the presence of a discontinuity, however, the ultrasonic beam F is interrupted and the failure of reception (by the transducer $R_1$) of a reflected beam, or in any case a strong disturbance of this beam, constitutes the indication of detection of a discontinuity D. According to the indirect technique, illustrated in FIG. 2 in which $E_2$ designates the transmitter transducer, however, the receiver transducer $R_2$ is arranged in the location in which the ultrasonic beam is expected if it is reflected by a discontinuity D.

A test method which involves mainly the diffraction of the ultrasonic beam and operates by observation or measurement of the times of flight associated with various trajectories of the ultrasonic waves combines the characteristics of the two foregoing techniques. According to this hybrid method (referred to as TOFD or Time Of Flight Diffraction), illustrated in FIG. 3, the waves of the diverging ultrasonic beam emitted by the transducer $E_3$ either directly reach the receiver transducer $R_3$ (lateral wave $O_A$ which is practically parallel to the surface of the object tested) or undergo a diffraction effect because of the presence of a discontinuity D in the material (waves $O_B$, $O_C$ diffracted by the extremities of the discontinuities), or reach the transducer $R_3$ after reflection from the opposite wall of the material (reflected wave $O_D$). The representation of the temporal position of the signals received by the transducer $R_3$ thus demonstrates, as shown in FIG. 4, the existence of a discontinuity inside the material: actually, on the time axis of FIG. 4 there are successively encountered a signal $S_A$ which corresponds to the lateral wave $O_A$, two signals $S_B$, $S_C$ which correspond to the two diffracted waves $O_B$, $O_C$, and a signal $S_D$ which corresponds to the reflected wave $O_D$ (in the absence of any discontinuity, exclusively the signals $S_A$ and $S_D$ would be received).

If the distance separating the transmitter transducer $E_3$ and the receiver transducer $R_3$ is referred to as 2S, the depth of the end of the discontinuity causing diffraction is denoted by the reference d, the lateral distance between this extremity $E_x$ and the median plane P situated at the same distance from the transducers is referred to as X, the respective distances between the extremity and the transducers $E_3$ and $R_3$ are referred to as M and L, and the ultrasonic speed (for example, in millimeters per second when the other distances are given in millimeters) is denoted by the reference c, the time T necessary for the ultrasonic wave to be diffracted by the extremity $E_x$ and subsequently received by the transducer $R_3$, i.e. for travelling the path (M+L), is given by the expression (1):

$$T = (M + L)/c \qquad (1)$$

$$T = \left(\sqrt{M^2} + \sqrt{L^2}\right)/c \qquad (2)$$

$$T = \left(\sqrt{(S+X)^2 + d^2} + \sqrt{(S-x)^2 + d^2}\right)/c \qquad (3)$$

The derivative of this expression (3) in relation to the variable X shows that the time T is minimum (and hence the detector signal is maximum) when X=0, i.e. when the extremity $E_x$ considered is in the median plane P situated at equal distances from the two transducers. Thus, carrying out the TOFD method consists in adjusting, once the signals $S_B$, $S_C$ indicating the presence of a discontinuity have been detected, the positions of the transducers $E_3$, $R_3$ (with a constant spacing 2S) so as to minimize the time T (i.e. the signal received is maximum).

The described TOFD method is disclosed, for example in "Vessel nozzle inner radius examinations using ultrasonic time-of-flight diffraction (TOFD)" by D. F. Loy and J. A. Vano issued at the "Vessel and Internals Inspection Conference" held in San Antonio (Tex., United States of America), Jul. 11–15, 1994.

The execution of this method, however, implies mobility of the transmitter-receiver assembly relative to the object to be tested by sliding on the surface of the latter in the plane of incidence containing the ultrasonic waves shown in FIG. 3, adjustment of the position of the transmitter and receiver transducers not being possible in the absence of such mobility. Unfortunately, the mechanical scanning required to realise this adjustment limits the data acquisition rate, prolongs the testing of objects of large surface area, and makes it more costly. The document U.S. Pat. No. 4,497,210 describes a phased array ultrasonic testing apparatus in which, in order to make easier the mobility, the mechanical scanning is replaced by an electronic one implemented on a single array probe. However, the distance between the transmitter transducer and the receiver one is not constant. Moreover, such mobility is nevertheless difficult to realize inside tubular objects to be tested.

In the course of such an adjustment the position of the transducers must be marked by means of localization means such as a position encoder. Actually, such localization is necessary if for easier interpretation of the test results for the object examined it is desired to form an image in which, for example one of the marking axes corresponds to the time of flight whereas the other axis, extending perpendicularly to the first one, corresponds to the position of the transmitter and receiver transducers, the amplitude of signals on that image being encoded in grey levels. Thus, the precision of any mechanical scanning system with position marking is limited and hence also the resolution of the image obtained.

Moreover, it has already been stated that displacement inside tubular objects is difficult to achieve, which also makes the marking of the position of the testing device difficult.

SUMMARY OF THE INVENTION

It is an object of the invention to provide a device for non-destructive testing which is particularly suitable for the testing of hollow tubular objects and in which the limitations mentioned above are mitigated.

To this end, the invention relates to a device of the kind set forth which is also characterized in that the transducer structure comprises an assembly of annular individual transducers which are juxtaposed in a coaxial fashion, and that the transmission and reception stages comprise means for the simultaneous selection of at least one transmitter transducer and at least one receiver transducer which are situated at a constant longitudinal distance from one another during the test and which form a transducer sub-assembly which can be displaced at will by electronic scanning along the longitudinal axis of the succession of transducers; alternatively, very similar embodiments are here, characterized in that the transducer structure comprises an annular array, which consists of an assembly of juxtaposed individual transducers, and that the transmission and receiving stages comprise means for the simultaneous selection of at least one transmitter transducer and at least one receiver transducer from the array, thus constituting a transducer sub-assembly which can be displaced at will by electronic scaning along the circular axis of the succession of transducers or characterized in that the transducer structure comprises two annular arrays, each of which consists of an assembly of circularly juxtaposed individual transducers, and that the transmission and reception stages comprise means for the simultaneous selection of at least one transmitter transducer from one of the arrays and at least one receiver transducer from the other array, thus constituting a transducer sub-assembly which can be displaced at will by electronic scanning along the circular axis of the succession of transducers.

Each of the structures of the device proposed, adapted for the testing of hollow tubular objects and particularly, but not exclusively, for the detection circumferential fissures, is also advantageous in that, thanks to the large number of transducer elements succeeding one another in a continuous fashion with a very small pitch, it enables accurate selection of a transmitter element, or a group of transmitter elements, and a receiver element, or a group of receiver elements, with extremely exact electronic marking of the position of the selected emitter and receiver elements. The execution of the TOFD method, being difficult in the case of objects such as notably the steam generator tubes of nuclear power plant circuits, is facilitated decisively, notably in applications involving a very large number of such objects to be tested.

In a first specific embodiment, the assembly or assemblies of individual transducers is or are realised as a one-piece unit, or in an alternative embodiment of the invention the assembly or assemblies is or are realised in the form of at least two identical elements which correspond to a complete ring in the assembled condition.

It is another object of the invention to provide an ultrasonic transducer structure incorporating one of the essential means of the invention.

To this end, the invention relates to an ultrasonic transducer structure comprising an assembly of individual transducers, characterized in that the transducers have an annular shape and are juxtaposed in a coaxial fashion, and that with the assembly there are associated means for the simultaneous selection of at least one transmitter transducer, or a group of transmitter transducers, and at least one receiver transducer, or a group of receiver transducers, which are situated at a constant longitudinal distance from one another during the test and form a transducer sub-assembly which can be displaced at will by electronic scanning along the longitudinal axis of the succession of transducers; alterativelly, in further embodiments of the invention an ultrasonic transducer structure is characterized in that it comprises an annular array, which consists of an assembly of individual transducers juxtaposed on the circumference of the ring, and that therewith there are associated means for the simultaneous selection of at least one transmitter transducer, or a group of transmitter transducers, and of at least one receiver transducer, or a group of receiver transducers, forming a transducer sub-assembly which can be displaced at will by electronic scanning along the circular axis of the succession of transducers or characterized in that it comprises two annular arrays, each of which consists of an assembly of individual transducers juxtaposed on the circumference of the ring, and that therewith there are associated means for the simultaneous selection, from one of the arrays, of at least one transmitter transducer, or a group of emitter transducers, and, from the other array, of at least one receiver transducer, or a group of receiver transducers, forming a transducer sub-assembly which can be displaced at will by electronic scanning along the circular axis of the succession of transducers.

Each of the structures thus formed is also suitable to receive from the non-destructive testing device for which it is intended the sequencing signals which enable the execution of electronic scanning of said transducer sub-assembly.

BRIEF DESCRIPTION OF THE DRAWING FIGURES

These and other aspects of the invention will be apparent from and elucidated with reference to the embodiments described hereinafter.

In the drawings:

FIG. 8 shows a second embodiment of the device of the invention, and the

DESCRIPTION OF THE INVENTION

Figure 6:
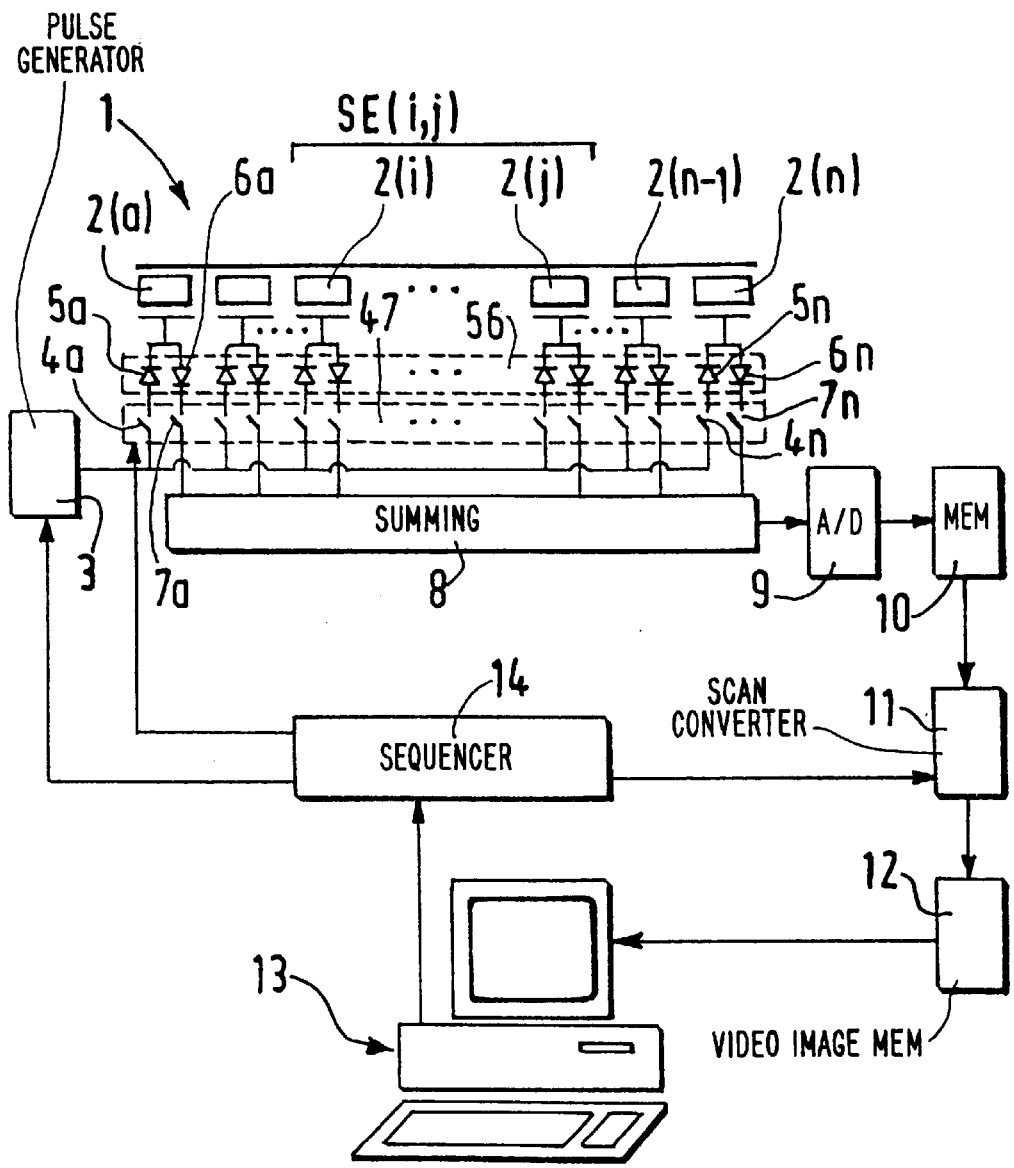
FIG. 6 shows a first embodiment of the device in accordance with the invention.
Figure 7:
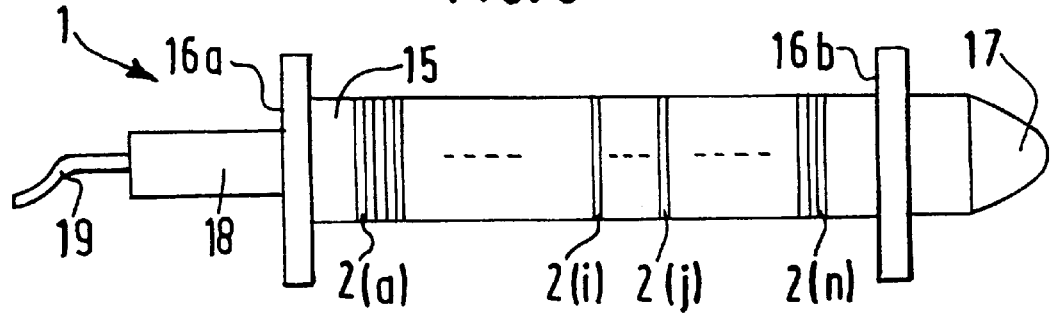
FIG. 7 is a more detailed representation of an ultrasonic transducer structure provided for the testing device shown in FIG. 6.

The device shown in FIG. 6 comprises first of all an ultrasonic transducer structure 1, consisting entirely of an assembly of annular individual transducers 2(a) to 2(n). These transducers are juxtaposed in a coaxial fashion so as to constitute together a type of cylindrical array. This array is implemented either as a single unit, or in the form of two assembled semi-annular elements, or as a larger number of identical elements corresponding to a complete ring in the assembled condition. The structure 1, shown in FIG. 7, is a probe comprising a cylindrical body 15 provided with the individual transducers 2(a) to 2(n). The probe also comprises two disc-shaped flanges 16a, 16b in the form of a disc for guiding it within the hollow tubular object to be tested, a nose 17 and a stud 18 for the connection of a cable 19 for supplying the probe with the excitation signals and for returning the receiving signals to the processing circuits of the testing device whereto the probe is connected.

By the connection cable 19, the n transducers are connected to a transmission stage which in this case comprises a low voltage (for example, 5 V) pulse generator 3, followed by n parallel transmission channels which are connected to the output of the generator and each of which comprises a series connection of a validation switch 4a to 4n and a high-voltage amplifier 5a to 5n in order to obtain, for example a voltage of 200 V. The n switches 4a to 4n form part of a channel validation circuit 47, and the n amplifiers 5a to 5n form part of an amplifier circuit 56. The outputs of the amplifiers of the circuit 56 are applied to the corresponding elementary transducers.

The n transducers are connected on the other hand to a receiving stage which in this case comprises n parallel receiving channels, each of which comprises a series connection of an amplifier 6a to 6n and a validation switch 7a to 7n. The n amplifiers 6a to 6n form part of the amplifier circuit 56 and the n switches 7a to 7n form part of the channel validation circuit 47. The outputs of the n receiving channels are applied to a summing circuit 8 which itself is succeeded by a series connection of an analog-to-digital converter 9, a memory 10 for storing all signals received during a complete image scan (for example, 128 lines of 1024 points each), a scan conversion circuit 11 for changing over, for example from the 128×1024 image to a displayed image comprising 256 lines of 256 points each, and a video image memory 12, the data stored in the latter memory being displayed on the screen of a computer 13. A sequencer 14 provides timing and synchronization of the various circuits, for which purpose it comprises connections to notably the pulse generator 3, the validation circuit 47, the scan conversion circuit 11, and the computer 13.

The device operates as follows. Under the control of the generator 3 which supplies excitation pulses of a few hundreds of volts, an annular transducer 2(i), or a small group of such transducers (for example, three or four), transmits a beam of ultrasonic waves to the zone to be tested. The selection of this or these transducers is enabled by the presence of the validation circuit 4i, 7i which, under the control of the sequencer 14, validates (by closing a switch or switches) the appropriate transmission channel or channels. The signals received in the course of the execution of the previously described TOFD method are received by an annular transducer 2(j) (or by a small group of such elementary annular transducers), after which they are amplified and added by means of the amplification circuit 5i, 6i and the summing circuit 8 respectively. The memory 10, when appropriately addressed, receives and stores, excitation by excitation, each signal obtained after summing and digitization by the analog-to-digital converter 9. The scan conversion circuit 11 reads the signals stored in the memory 10 and composes an image on the basis thereof by adjusting the scale factor in X and in Y and by performing a zoom operation, if any (the latter operations are made possible by resampling of the signals acquired and by interpolation). The new image obtained after scan conversion is stored in the video image memory 12, after which it is displayed on the screen of the computer 13. In conformity with the above description of the TOFD method, the detection of any discontinuities in the object zone to be tested is optimized by electronic scanning by displacement of the sub-assembly SE(i,j), formed by the transmitter transducer or the group of transmitter transducers and the receiving transducer or the group of receiving transducers, while keeping their spacing constant within said sub-assembly.

Figure 8:
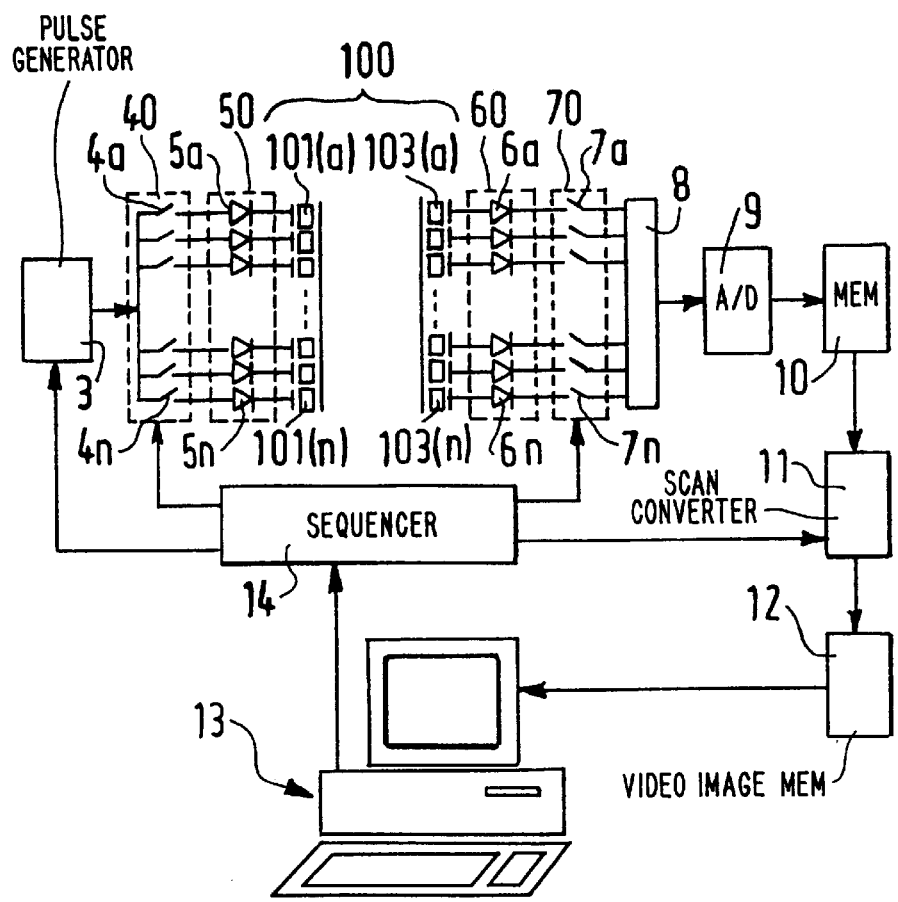
Figure 9:
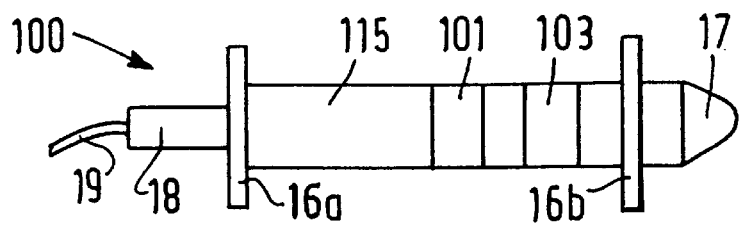
FIGS. 9 and 10 are more detailed representations of two embodiments of an ultrasonic transducer structure provided for the testing device shown in FIG. 8.

Another embodiment of the device in accordance with the invention, shown in FIG. 8, comprises a transducer structure 100. This structure 100, shown in FIG. 9, is a probe comprising a cylindrical body 115 on which there are mounted two annular piezoelectric arrays 101 and 103, each of which consists of an assembly of elementary transducers 101(a) to 101(n) and 103(a) to 103(n) which are juxtaposed on the circumference of the ring. As before, each of these arrays can be realized either as a single unit or as two or more identical corresponding elements which constitute a complete ring, when assembled to be arranged on the body 115. The structure 100 also comprises, as before, two flanges 16a, 16b in the form of a disc for guiding the probe inside the hollow tubular object to be tested, a nose 17, and a stud 18 for connection of the cable 19 for connection to the testing device.

In this transducer structure 100, one of the arrays, for example the array 101 formed by the n transducers 101(a) to 101(n), is dedicated to the transmission and the other array (the array 103 formed by the transducers 103(a) to 103(n)) is dedicated to the reception. The n transducers 101(a) to 101(n) are connected to a transmission stage which comprises, as before, the low-voltage pulse generator 3 (for example, 5 V), followed by n parallel transmission channels which are connected to the output thereof and each of which comprises a series connection of a validation switch 4a to 4n and a high-voltage amplifier 5a to 5n. The n switches 4a to 4n form part of a channel validation circuit 40 and the n amplifiers 5a to 5n form part of an amplifier circuit 50. The outputs of said amplifiers of the circuit 50 are applied to the corresponding elementary transducers.

The n transducers 103(a) to 103(n) of the array 103 dedicated to the reception are connected to a receiving stage which comprises n parallel receiving channels, each of which comprises a series connection of an amplifier 6a to 6n and a validation switch 7a to 7n. The n amplifiers 6a to 6n form part of an amplifier circuit 60 and the n switches 7a to 7n form part of a channel validation circuit 70. The outputs of the n receiving channels are applied, as before, to the summing circuit 8 which itself is followed by a series connection of the analog-to-digital converter 9, the memory 10 for storing all signals during a complete image scan by the scan conversion circuit 11, and the video image memory 12, the data stored in the latter memory being displayed on the screen of the computer 13. The sequencer 14 provides the timing and synchronization of the various circuits, i.e. the pulse generator 3, the validation circuits 40 and 70, the scan conversion circuit 11, and the computer 13. The operation of the device is the same as that of the device of FIG. 6, except that n transducers are now dedicated to the transmission and n distinct transducers are dedicated to the reception.

Figure 10:
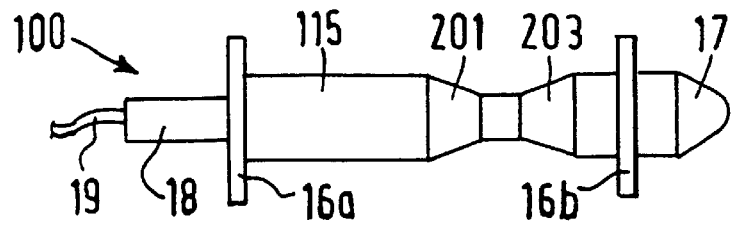

It is to be noted that the present invention is by no means limited to the embodiments described and shown, and that many alternatives can be proposed on the basis thereof. In particular the arrays 101 and 103 in FIG. 9 have a cylindrical shape but, as appears from FIG. 10 which shows an alternative embodiment of the probe, there may be provided two arrays 201 and 203 which have a truncated shape and which enable better orientation of the ultrasonic waves transmitted to the object zone to be tested. The other elements are not modified and are denoted by the same references. It is also possible that the transducer structure comprises no longer two annular arrays but only one with an assembly of circularly juxtaposed dividual transducers, the simultaneous selection being then made on this single array in order to constitute a transducer sub-assembly which can be displaced at will by electronic scanning along the circular axis of the succession of transducers.

Moreover, it is to be noted that the invention does not relate exclusively to devices for non-destructive testing as described above, but also to transducer structures provided with one of the essential means of the invention.

Figure 1:
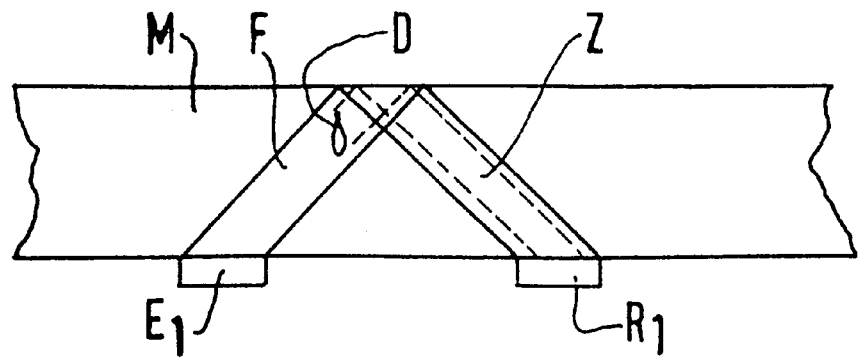
FIGS. 1 and 2 illustrate two distinct known techniques for the non-destructive testing of materials.
Figure 2:
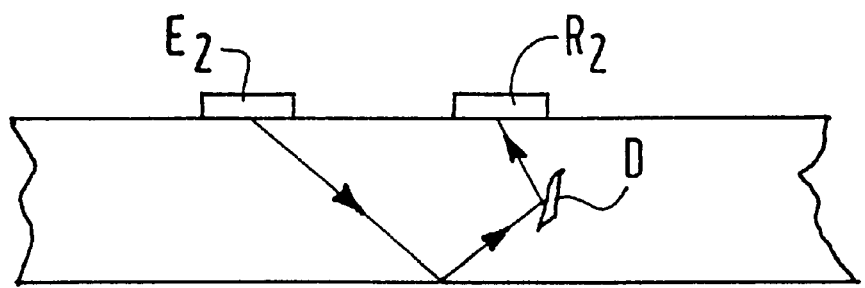
Figure 3:
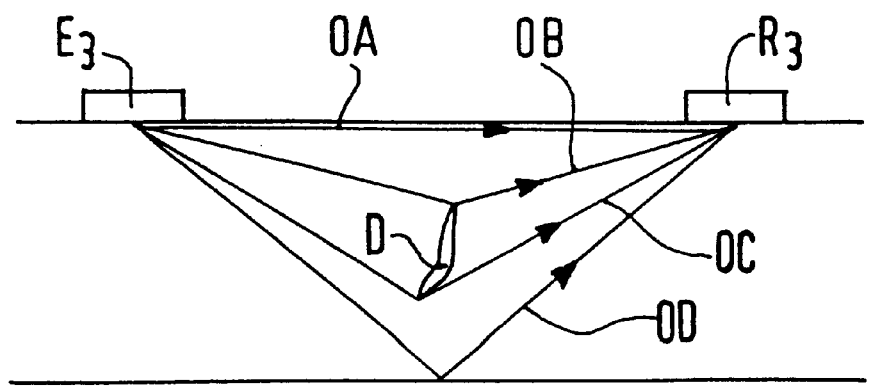
FIGS. 3, 4 and 5 illustrate a hybrid, third technique (also known) which combines the characteristics of the first two techniques.
Figure 4:
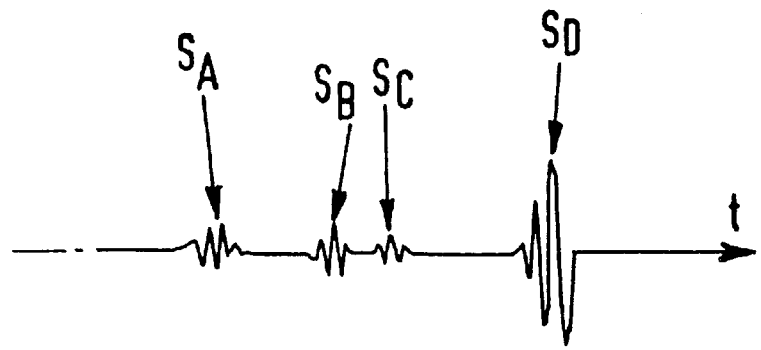
Figure 5:
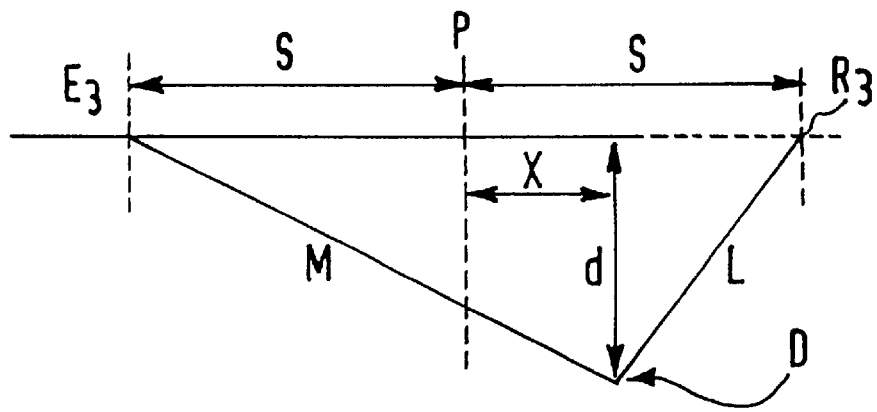
Figure 11:
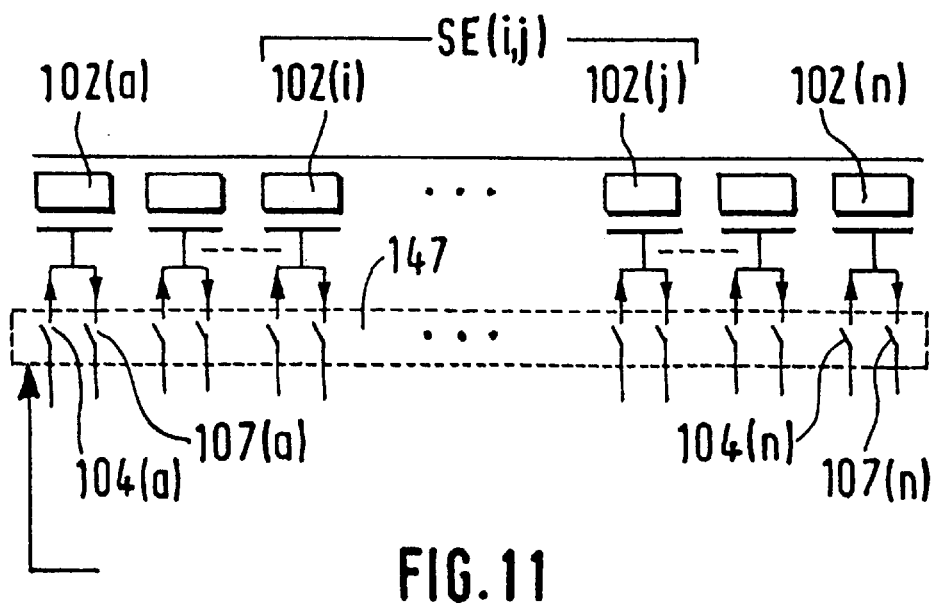
FIG. 11 shows an embodiment of an ultrasonic transducer structure incorporating an essential means of the invention, which in this case corresponds to the embodiment of the device shown in FIG. 6.

For example, in the case of the device shown in FIG. 6, the probe could comprise, as appears from FIG. 7, only the transducers 2(a) to 2(n), or could also comprise, as appears from the embodiment shown in FIG. 11 and in association with each of the transducers now denoted by the references 102(a) to 102(n), a validation circuit 147 which comprises 2n switches 104(a) to 104(n) and 107(a) to 107(n) which respectively enable validation or non-validation of a transducer or a group of transducers in the transmission mode (the switches 104(a) to 104(n)) and of a transducer or a group of transducers in the receiving mode (the switches 107(a) to 107(n)). Thus, as before, a given transducer sub-assembly SE(i,j) is selected which is displaceable at will by electronic scanning (i.e. without physical displacement), transversely of the object zone to be tested and in such a manner that in the course of the test the transmitter transducer or transducers and the receiver transducer or transducers remain at a constant distance from one another. When the transducer structure thus formed is connected to the testing device (which in this case no longer comprises the switches because they are incorporated in the transducer structure), it only need be supplied with the sequencing signals effectively enabling the execution of the scanning operation, i.e. the closing or opening of each of the switches in a distinct manner so as to ensure the displacement (without movement) of the transducer sub-assembly SE(i,j). This embodiment also concerns the other described probes which, as for this embodiment of FIG. 11, can incorporate the validation switches of the transmitter and receiver transducers.

I claim:

1. A device for the non-destructive testing of hollow tubular objects by means of ultrasound, said device comprising:
   a transducer structure having a succession of individual transducers disposed along an axis;
   a transmission stage for stimulating the transmission of ultrasonic waves by excitation of said transducer structure;
   a reception stage for the reception of signals derived from ultrasonic signals received by said transducer structure; and
   means for the simultaneous selection of at least one of said individual transducers as a transmitter transducer and at least one different one of said individual transducers as a receiver transducer, a selected transmitter transducer and a corresponding selected receiver transducer being situated at a constant distance from one another during a test, thereby forming a transducer sub-assembly displaceable by electronic scanning along the axis of the succession of transducers, said means permitting selection of an individual transducer either as a transmitter transducer or a receiver transducer.

2. The device as claimed in claim 1, wherein said transducer structure includes an assembly of annular individual transducers which are juxtaposed in a coaxial fashion, and wherein said transducer sub-assembly is displaceable along the longitudinal axis of the succession of transducers.

3. The device as claimed in claim 1, wherein said assembly of individual transducers is a one-piece unit.

4. The device as claimed in claim 1, wherein said assembly of individual transducers is at least two identical elements which correspond to a complete ring in the assembled condition.

5. The device as claimed in claim 1, wherein said transducer structure includes an annular array, and wherein said transducer sub-assembly is displaceable along the circular axis of the succession of transducers.

6. The device as claimed in claim 5, wherein said assembly of individual transducers is a one-piece unit.

7. The device as claimed in claim 5, wherein said assembly of individual transducers is at least two identical elements which correspond to a complete ring in the assembled condition.

8. The device as claimed in claim 1, wherein said transducer structure includes two annular arrays, each of which consists of an assembly of circularly juxtaposed individual transducers, and wherein said means selects at least one transmitter transducer from one of the arrays and at least one receiver transducer from the other array, and wherein said transducer sub-assembly is displaceable along the circular axis of the succession of transducers.

9. The device as claimed in claim 8, wherein said assembly of individual transducers is a one-piece unit.

10. The device as claimed in claim 8, wherein said assembly of individual transducers is at least two identical elements which correspond to a complete ring in the assembled condition.

11. The device of claim 1 wherein the axis of the transducers is coincident with an axis of a tube.

12. The device as claimed in claim 1, wherein said transducer structure includes an assembly of individual transducers which are juxtaposed along the same axis, the axis being the longitudinal axis of the structure.

13. The device as claimed in claim 1, wherein said transducer structure includes an assembly of individual transducers which are juxtaposed along the same axis, the axis being the circumference of said structure.

14. The device as claimed in claim 1, wherein said transducer structure includes two annular arrays, each of which includes an assembly of circularly juxtaposed individual transducers, and said means selects at least one transmitter transducer and at least one receiver transducer, each from one of the arrays.

15. An ultrasonic transducer structure comprising:
   a succession of individual transducers disposed along an axis; and
   means for the simultaneous selection of at least one of said individual transducers as a transmitter transducer and at least one different one of said individual transducers as a receiver transducer, a selected transmitter transducer and a corresponding selected receiver transducer being situated at a constant distance from one another during a test, thereby forming a transducer sub-assembly displaceable by electronic scanning along the axis of the succession of transducers, said means permitting selection of an individual transducer either as a transmitter transducer or a receiver transducer.

16. The ultrasonic transducer structure as claimed in claim 15, including two annular arrays, each of which consists of an assembly of individual transducers juxtaposed along a diameter of said structure.

17. The structure of claim 15 wherein the axis of the transducers is coincident with an axis of a tube.

18. The ultrasonic transducer structure as claimed in claim 15, wherein said transducers have an annular shape and are juxtaposed in a coaxial fashion and said transducer sub-assembly is displaceable along the longitudinal axis of the succession of transducers.

19. The ultrasonic transducer structure as claimed in claim 15, wherein said assembly of individual transducers are juxtaposed on the circumference of the ring, and said transducer sub-assembly is displaceable along the circular axis of the succession of transducers.

20. The ultrasonic transducer structure as claimed in claim 15, including two annular arrays, each of which includes an assembly of individual transducers juxtaposed on the circumference of the ring, and wherein said transducer sub-assembly is displaceable along the circular axis of the succession of transducers.

21. The ultrasonic transducer structure as claimed in claim 15, wherein said assembly of individual transducers are juxtaposed along the same axis, said axis being the longitudinal axis of said structure.

22. The ultrasonic transducer structure as claimed in claim 15, wherein said assembly of individual transducers are juxtaposed along the same axis, said axis being a circumference of said structure.

23. An ultrasonic transducer structure comprising:
   a plurality of individual annular transducers juxtaposed coaxially, but not concentrically; and
   a selection circuit arranged to select at least one of said transducers as a transmitter transducer and at least one different one of said transducers as a receiver transducer in order to form a transducer subassembly.

24. The structure of claim 23 wherein the transducers are fixed to a solid support so that the at least one transmitter transducer and at least one receiver transducer are situated at a constant longitudinal distance from each other during test.

25. The structure of claim 24 wherein the solid support is translatable along an axis of the transducers to scan a hollow tube.

26. The structure of claim 25 wherein the solid transport, the transducers, and the selection circuit are disposed on a probe which is insertable into an interior of the hollow tube.

27. The structure of claim 23 wherein the selection circuit is arranged to scan the transducers and create a succession of sub-assemblies for TOFD testing of a tube.

* * * * *